(12) United States Patent
Horigane et al.

(10) Patent No.: US 7,067,834 B2
(45) Date of Patent: Jun. 27, 2006

(54) APPARATUS AND PROCESS FOR SECURING, ANALYZING AND SORTING MATERIALS, AND SORTED PRODUCTS

(75) Inventors: Akira Horigane, Tsukuba (JP); Masaaki Horiguchi, Tsukuba (JP)

(73) Assignee: Tsukuba Food Science, Inc., Ushiku (JP)

( * ) Notice: Subject to any disclaimer, the term of this patent is extended or adjusted under 35 U.S.C. 154(b) by 350 days.

(21) Appl. No.: 10/375,377

(22) Filed: Feb. 27, 2003

(65) Prior Publication Data

US 2004/0074822 A1    Apr. 22, 2004

(30) Foreign Application Priority Data

Aug. 5, 2002    (JP) .............................. 2002-227905

(51) Int. Cl.
*B07C 5/00*    (2006.01)
(52) U.S. Cl. ...................................... 250/576
(58) Field of Classification Search ................. 422/99; 436/172; 250/338.1
See application file for complete search history.

(56) References Cited

U.S. PATENT DOCUMENTS 5,686,313 A    11/1997   Sitte et al.
6,471,814 B1 *  10/2002   Ito et al. ...................... 156/247

FOREIGN PATENT DOCUMENTS

DE    36 24 420    4/1987
DE    197 14 975   12/1997
EP    1 126 268    8/2001
GB    2 144 366    3/1985

* cited by examiner

*Primary Examiner*—David Porta
*Assistant Examiner*—Marcus Taningco
(74) *Attorney, Agent, or Firm*—Flynn, Thiel, Boutell & Tanis, P.C.

(57) ABSTRACT

An apparatus for securing, analyzing and sorting materials, which allows such procedures as analysis and sorting of materials present as independent pieces at a high efficiency and a high accuracy, by securing individual pieces 5 of materials in receptacles 4 of a holder 1 at a definite posture using a light-hardenable adhesive at a uniform hardening strength and a uniform but brief hardening time by cold hardening under identical hardening conditions without causing denaturation of the material, wherein the receptacles 4 are arranged on the holder 1 in a definite arrangement and a definite posture, whereby it is able to process each individual material piece after the hardening of the adhesive, by, for example, cutting and so on, to uniformly form on each material piece an analyzing surface for which the analysis is performed. Each material piece 5 is bonded and fixed onto an inner wall of the receptacle 4 using a light ray-hardenable adhesive 7 by irradiating a light ray 8 thereonto to effect hardening of the adhesive at normal temperatures. The resulting holder 1 having the fixed material pieces is mounted on an analyzing unit 12 to subject each material piece to a spectrometric analysis by irradiating it with an electromagnetic ray 15. Then, the holder 1 having the analyzed material pieces is set on a sorting device 22 to sort the analyzed material pieces, in which the material pieces are dispensed by operating dispenser rods 24 based on the analysis results.

10 Claims, 12 Drawing Sheets

Fig. 11(a)
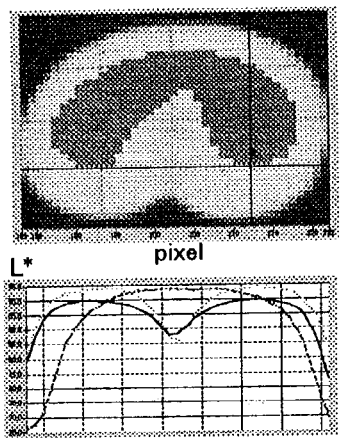
Fig. 11(b)
Fig. 11(c)
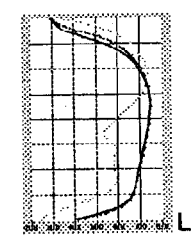
Fig. 11(d)
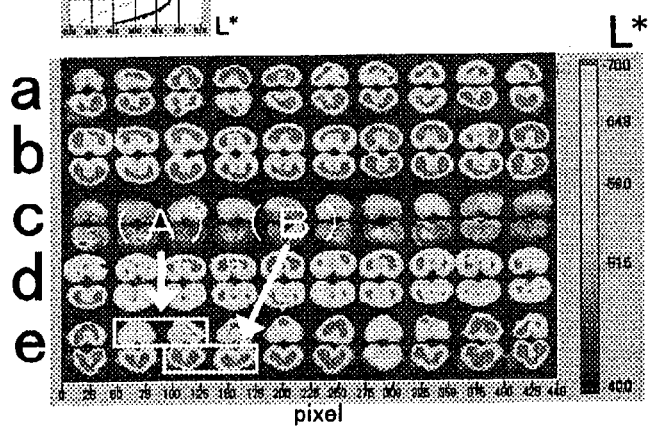

APPARATUS AND PROCESS FOR SECURING, ANALYZING AND SORTING MATERIALS, AND SORTED PRODUCTS

FIELD OF THE INVENTION

The present invention relates to an apparatus and process for securing individual pieces of materials in a definite arrangement and a definite posture for realizing such treating processes as analysis, sorting and so on of individual pieces of materials; to an apparatus and process for realizing analysis or sorting of the resulting secured individual pieces of materials; and to the sorted products obtained thereby.

BACKGROUND OF THE INVENTION

For analyzing materials present as individual pieces, for example, biological material, such as seeds of cereals and so on, and others, by, for example, spectroscopic analysis and the like, by irradiation with an electromagnetic ray, such as an infrared ray or so on, each individual piece of material is first secured on a sample holder and the analysis is performed on the so-secured sample of the material piece. In the case of analyzing, for example, seeds of a plant, seed samples are secured in receptacles formed on a sample holder in a definite arrangement and a definite posture, whereupon the analysis is performed on, for example, an analyzing surface formed, if necessary, on each seed sample by processing it by, for example, cutting and/or grinding. The analysis is performed in general in such a way that a plurality of receptacles for receiving each sample, such as sample compartments, are formed on a sample holder and each sample is secured in each of the receptacles, whereupon the so secured samples are subjected to the same analysis operation simultaneously or successively to obtain the analysis results for these samples in one single analysis course.

Heretofore, analysis samples were secured on the sample holder in general using an adhesive or a filler. However, this prior art method suffers from a problem that a uniform solidification time and uniform adhesion strength of the adhesive or filler are difficult to attain for all the samples.

Use of an adhesive in the form of a solution in a solvent will require considerable time for the removal of the solvent with concomitant reduction of the accuracy of the analysis due to contamination of the sample by the solvent.

In contrast thereto, use of an adhesive of a hardening type requires admixing of a hardening agent to the adhesive to initiate hardening, which accompanies a problem that introduction of the adhesive into a plurality of receptacles is not easy, often causing differences in the hardening conditions due to a possible discrepancy upon the introduction of the adhesive, resulting in an unequal hardening aspect for different samples. When the hardening is effected within a shorter period of time, the processibility of the sample deteriorates and, when the hardening takes a longer period of time, an extended time is required for attaining the requisite adhesion strength, resulting in a lower efficiency of the analysis.

When a cold-hardening adhesive, such as those based on an epoxy resin, is used, a proper analyzing surface, on which the analysis is performed, is difficultly formed by cutting and/or grinding the sample due to difficulty in maintaining the definite secured state of the sample steadily, since a cold hardening adhesive requires a considerable period of time for hardening at normal temperatures and complete hardening will hardly be attained at normal temperatures. When heating is incorporated for attaining complete hardening, the sample may be apt to suffer from denaturation from the heat.

On the other hand, when an instantaneously hardening adhesive is used, it exhibits a high permeability into organic matter and may cause denaturation of the sample, in addition to the problem of easy dripping down from the interspace between the sample and the receptacle inner wall due to its low viscosity.

SUMMARY OF THE INVENTION

An object of the present invention is to provide an apparatus and a process for securing individual pieces of materials, which can allow such procedures as analysis and sorting of the material pieces at a high efficiency and a high accuracy, by securing individual pieces of materials in receptacles of a holder at a definite posture using an energy ray-hardenable adhesive, which can harden at a uniform strength in a uniform but brief hardening time at normal temperatures by irradiation of an energy-ray, under identical hardening conditions without causing denaturation of the material, so as to permit equal definite processing of each individual material piece in a reliable manner by, for example, cutting and/or grinding for forming thereon an analyzing surface on which the analysis is performed.

Another object of the present invention is to provide an apparatus and a process for analyzing individual pieces of materials, which can afford the realization of an qualitative and/or quantitative analysis of each material piece at a high efficiency and a high accuracy under reduction of computer load for controlling, estimating and processing the operation of each specific analysis item and the analysis data, by limiting the analysis site on the analyzing surface, under the use of the apparatus and the process for securing individual pieces of materials mentioned above.

A further object of the present invention is to provide an apparatus and a process for sorting individual pieces of materials as well as sorted products obtained thereby, which can afford the realization of sorting of the material pieces at a high efficiency and a high accuracy under incorporation of, if necessary, a multiplication and/or an amplification of the sorted individual piece showing the content of a useful component.

For attaining the above objects, the present invention consists of the following apparatuses and processes for securing, analyzing and sorting individual pieces of materials:

(1) An apparatus for securing individual pieces of materials in a definite arrangement and a definite posture, comprising an energy ray-permeable holder provided with a plurality of receptacles disposed in a definite arrangement and a definite posture for receiving each individual piece of material and an energy ray-hardenable adhesive interposed between each individual piece of material and inner wall of the corresponding receptacle for fixing the material piece in the receptacle.

(2) The apparatus as defined in the above (1), wherein the holder is provided over its surfaces with a reflective layer of a substance adapted to reflect the energy ray.

(3) The apparatus as defined in the above (2), wherein, in the case where individual pieces of materials secured on the holder are to be analyzed by irradiation of an electromagnetic ray thereonto, the reflective layer on the holder comprises, at least on the side on which the electromagnetic ray is irradiated, a layer of a substance which will not cause analysis noise.

(4) An apparatus for analyzing individual pieces of materials, comprising an apparatus for securing individual pieces of materials in a definite arrangement at a definite posture as defined in any one of the above (1) to (3) and an analyzing unit for analyzing each individual piece of material which has been secured on the holder.

(5) An apparatus for sorting individual pieces of materials, comprising an apparatus for securing individual pieces of materials in a definite arrangement at a definite posture as defined in any one of the above (1) to (3), an analyzing unit for analyzing each individual piece of material which has been secured on the holder as defined in the above (4), and a sorting device operative to sort individual pieces of materials based on the results of the analyses.

(6) A process for securing individual pieces of materials in a definite arrangement at a definite posture, comprising the steps of receiving individual pieces of materials at a definite posture, each in each of a plurality of receptacles provided on an energy ray-permeable holder in a definite arrangement and a definite posture and bonding each individual piece of material onto an inner wall of the corresponding receptacle with an energy ray-hardenable adhesive by irradiating an energy ray onto the adhesive to harden it to thereby fix the material piece in the receptacle.

(7) The process as defined in the above (6), wherein the holder is provided over its surfaces with a reflective layer of a substance adapted to reflect the energy ray.

(8) The process as defined in the above (7), wherein, in the case where individual pieces of materials secured on the holder are to be analyzed by irradiation of an electromagnetic ray thereonto, the reflective layer on the holder comprises, at least on the side on which the electromagnetic ray is irradiated, a layer of a substance which will not cause analysis noise.

(9) A process for analyzing individual pieces of materials, comprising the step of performing the analysis for each individual piece of material which has been secured at a definite posture by the process as defined in any one of the above (6) to (8).

(10) A process for analyzing individual pieces of materials which have been secured at a definite posture in receptacles of a holder of an apparatus as defined in any one of the above (1) to (3), which receptacles are disposed in a definite arrangement at a definite posture, comprising the steps of forming on each individual piece of material an analyzing surface and performing the analysis by irradiation of an electromagnetic ray onto the analyzing surface.

(11) The process as defined in the above (10), wherein the analyzing surface consists of one or more planes which extend in horizontal and/or in any other inclined plane(s).

(12) A process for analyzing individual pieces of materials, each having an analyzing surface, comprising the steps of transferring a superficial layer of the analyzing surface an individual piece of material onto any other surface and effecting the analysis by irradiation of an electromagnetic ray onto the transferred layer.

(13) A process for sorting individual pieces of materials, comprising the step of performing sorting operations for each individual piece of material based on the results of analyses obtained by a process for analyzing individual pieces of materials as defined in any one of the above (9) to (12).

(14) The process for sorting as defined in the above (13), wherein it comprises a further step of multiplication and/or amplification of the sorted individual piece.

(15) A sorted product which is obtained by a process for sorting as defined in the above (13) or (14).

BRIEF DESCRIPTION OF THE DRAWINGS

FIGS. 11a, 11b and 11c show an enlarged computer-processed lightness distribution image on a cut face of an endosperm of a seed of wheat, lightness distribution curves along three horizontal lines on the image and lightness distribution curves along three vertical lines on the image, respectively.

FIG. 11d shows an lightness distribution image on cut faces through an endosperm of five groups of seeds of wheat by an analysis using a two-dimensional calorimeter in a compiled representation in which each cut face image is arranged so as to correspond to each corresponding receptacle on a corresponding sample holder.

DETAILED DESCRIPTION OF THE INVENTION

Figure 1:
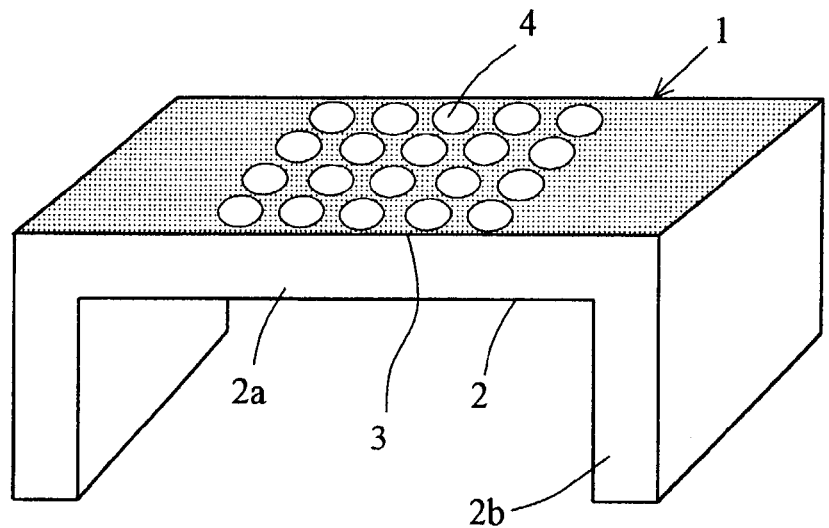
FIGS. 1a and 1b each show an embodiment of the apparatus for securing individual pieces of materials according to the present invention, each in a perspective view in an off duty state (material pieces are absent) and in an on duty state, respectively.
Figure 1:
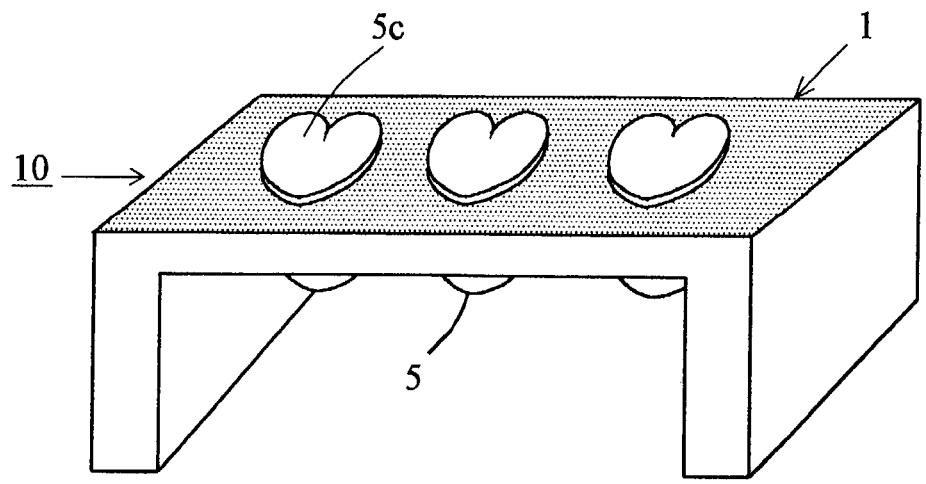

The materials to be dealt with by the securing technique in accordance with the present invention should be in a form of individual pieces to be subjected to the processes of such techniques as analysis and sorting according to the present invention. Such materials may be exemplified by living organisms, organic and inorganic substances, chemicals and printed examples matter. Specific examples thereof include seeds, stalks, leaves and roots of plants; agricultural products; tissues of plants and animals, including humans; and food products. Materials in the form of a powder, liquid or paste may also be included, so long as they can be formed into individual pieces by an adequate technique, including compacting, binding with a binding agent, freezing and encapsulation. Materials capable of being subjected to multiplication under sorting by having resort to, for example, differences in the distribution of specific components in the material, such as plant seeds, are preferable to be dealt with by the securing technique according to the present invention.

Such securing techniques according to the present invention can be employed in such application fields as analysis and sorting of examination samples. For the techniques of analysis, there may be employed, for example, spectroscopic analyses including those using visible light, infrared rays, ultraviolet rays, fluorescent rays, Raman effect, X-rays and two-dimensional colorimetry; techniques employing numeric computation, such as image analysis with image inputting function, Laser Abrasion-ICP mass spectrometric analysis, mass spectroscopic analyses and NMR-techniques; techniques for imaging devices including MRI and ultrasonic diagnosis devices, for microscopes (including electron microscope), for image readers including television and image scanners; and analyses by observation, determination and recording on images produced by means of holographs, as well as visual analysis.

The apparatus for securing individual pieces of materials is constructed such that a plurality of receptacles for receiving each material piece therein are disposed on a holder in a definite arrangement and a definite posture and the material pieces are secured therein at a definite posture by being bonded on the inner wall of the receptacle with an energy ray-hardenable adhesive placed in the interspaces between the material piece and the inner wall of the receptacle and are fixed by causing the adhesive to harden at normal temperatures by irradiation of an energy ray, such as light rays, onto the adhesive.

The holder is made of an energy-ray permeable substance. Here, the "energy ray" means a radiant ray used for hardening adhesives, for example, an electromagnetic ray, such as visible light, ultraviolet light and X-rays; radioactive rays; an electron beam; and so on. The holder may not necessarily be permeable for all these energy rays, but may only be required to exhibit permeability for such energy rays that are effective to harden the applied adhesive when irradiated thereonto. Thus, in the case where the adhesive is caused to harden by irradiation of a visible light, the holder may be made of a transparent plastic material. For the material of the holder, there may preferably be used a polymer resin, such as an acrylic resin, polycarbonate resin or the like, since thereby, formation of the receptacles on the holder can easily be attained by molding the holder or by a mechanical after-processing.

The receptacles for receiving individual pieces of materials are formed on the holder in a definite arrangement at a definite posture so as to permit the receiving of each individual material piece by being inserted therein at a definite posture. The receptacles may preferably each be formed in a configuration nearly corresponding to that of the individual material piece. Here, the configuration of the receptacle may not necessarily correspond to the entire shape of the individual material piece, but may be permitted to nearly correspond only to the shape of the individual piece of the part required for attaining the securing. For instance, when seeds of a plant are to be secured, they may be secured on the apparatus for securing individual pieces of material in such a way, that they are provisionally fixed on a fitting plate with a fixing means, such as a double-sided adhesive tape, and are then secured on the securing apparatus in this pre-fixed state in such a manner that the part of the seed necessary for the growth of the plant, namely, the portion including the embryo, is maintained without being subjected to any damage by retaining this part of the seed outside the receptacle and holding the body part of the seed, namely, the part of the endosperm, insertedly in the receptacle, in order to avoid misrecognition of the mutual correspondence with the analyzing surface to be used for effecting the analysis after it has been formed on the seed by cutting and/or grinding, before the seed is finally secured by causing the adhesive placed in the interspaces between the endosperm part and the inner wall of the receptacle to harden so as to permit the formation of the analyzing surface thereon.

The receptacles may preferably be formed so as to leave some interspace between the inserted individual material piece and the inner wall of the receptacle. The size of the interspace may favorably be such that any possible deviation in the outer span or diameter of individual pieces can be tolerated. The plurality of receptacles formed on the holder may each be present either independently of each other or in a form partly joined with each other.

The holder should be provided with a number of receptacles for receiving a number of individual pieces of materials and for permitting their analysis at the same time. It is preferable here to dispose a number of receptacles side by side on the same face of the holder, in order to permit simultaneous or successive analysis of individual pieces of materials. For example, in the case where individual seeds of a plant are to be analysed, it is preferable to form the receptacles in such a way, that the seeds are received in the receptacles in a posture in which the side of the seed including the embryo is held in the receptacle on the side not used to effect the analysis and the other side of the seed composed of the endosperm is held under protrusion from the receptacle, so as to permit the processing of each seed in an assigned site of the endosperm part on the same plane at an equal and definite posture by cutting and/or grinding to form an analyzing surface after the seeds have been securely fixed, whereby an analysis process can be performed on the analyzing surface under the same condition. In particular, in the case where the analysis is performed by reaction with an analyzing reagent, such as ninhydrin, iodine/potassium iodide reagent or so on, or with a dyeing reagent, such as a fluorescent probe or so on, the embryo side of the seed should preferably be held on the side of the receptacle not used for such analysis reaction.

The holder may preferably be provided over its surfaces with a reflective layer of a substance adapted to reflect the energy ray. The reflective layer is made of a substance adapted to reflect the energy ray, wherein the substance may preferably have at the same time a property which does not cause the occurrence of analysis noise. If a reflective layer is made of a substance which causes the occurrence of analysis noise, it is favorable to coat thereon a layer of a substance not causing analysis noise to reduce the occurence of analysis noise. Since the holder is made of a substance which permeates energy rays, the energy ray-hardenable adhesive will harden by causing a hardening reaction upon irradiation of an energy ray thereon by permeating into the adhesive through the holder. Here, however, those portions of the energy ray permeating through the portion of the holder devoid of the adhesive are not utilized for the reaction. In addition, the adhesive present on the rear side of the holder opposite to the side irradiated with the energy ray will be subjected to the hardening reaction at a retarded rate. However, by providing the holder with an energy ray reflective layer, the hardening reaction is promoted by the portion of the energy ray reflected from the layer to the reverse side and penetrating into the adhesive, attaining thereby a higher reaction efficiency and higher uniformity of reaction over the entire extent thereof.

In spectroscopic analysis using the apparatus according to the present invention, the holder may often act as a source of analysis noise. However, when a reflective layer is formed over the holder surface by coating with a layer of a metal which may, in most cases, not be contained in the material to be analysed, such as gold, the occurrence of analysis noise can favorably be avoided and increased analysis accuracy is attained. In the case where the reflected energy ray causes analysis noise, such as in the case of using a two-dimensional colorimeter, it is preferable to coat (laminate) the holder surface with a black layer, such as a layer of carbon, by vapor deposition. Coating with a substance contributive to reducing the analysis noise may also be preferable. It is enough that the thickness of the reflective layer may be only that enabling reflection of the energy rays and, in the case of coating with a gold layer, a thickness in the range of some tens μm to several hundreds μm may be mentioned.

The adhesive to be used for fixedly securing each individual material piece may be of an energy ray-hardenable type. Typical of such adhesives may be those of the light-hardenable type which will harden by irradiation with a visible light or an ultraviolet light, though other adhesives, which will harden by irradiation of an energy ray, such as electromagnetic rays, radioactive rays and electron beams, may also be employed. For such energy ray-hardenable adhesives, there may be recited, for example, those based on radical polymerization, such as acrylates, urethane-acrylates, epoxy-acrylates, melamine-acrylates, acrylic acrylates and unsaturated polyesters; those based on thiol/-ene addition; and those based on cationic polymerization.

Among such adhesives, those which comprise a polymerizable oligomer of the resins mentioned above, monomers serving as reactive diluents and an energy ray-polymerization initiator generating an activation source, such as a free radical, by absorbing the energy rays are preferred. The adhesive may further comprise additives, such as a filler, stabilizer and so on, in addition to the above ingredients. For the adhesive, those which are commercially available may be used, wherein those which are available as fillers or bonding materials for dental applications may be utilized as such, with particular preference to those used as dental fillers.

The process for securing individual pieces of materials according to the present invention comprises process steps constituted of a step of receiving individual pieces of materials at a definite posture, each in each of a plurality of receptacles provided on the holder in a definite arrangement and a definite posture, and a step of bonding each individual material piece onto an inner wall of a corresponding receptacle with an energy ray-hardenable adhesive placed in interspaces between each material piece and the inner wall of the correponding receptacle by irradiating an energy ray onto the adhesive to harden it and thereby cause the material piece to be secured fixedly in the receptacle. While the interspaces may be different in each case in their thicknesses or gap sizes due to possible fluctuations in the diametral size of each individual material piece, the strength of adhesion of individual pieces of materials onto the inner wall of the receptacle may be kept at an equal level by using an adhesive exhibiting better filling ability so as to have a sufficient degree of filling of the interspaces. Here, the interspaces are not necessarily filled with the adhesive completely, but may be permitted to fill them up to a certain degree, so long as the strength of adhesion reaches a definite level.

In the bonding step for bonding each individual material piece onto the inner wall of a corresponding receptacle, the energy ray-hardenable adhesive is caused to initiate its hardening reaction by irradiating it with an energy ray through the energy ray permeable holder. After a certain reaction time has elapsed while being irradiated with an energy ray of a certain energy level, the hardening reaction is completed, whereby a contemplated definite adhesion strength is attained. When the holder is provided over its surfaces with a reflective layer adapted to reflect the energy ray, the hardening time can be reduced with the simultaneous attainment of a uniform hardening reaction over the entire extent of the adhesive. By effecting bonding of the individual pieces of materials onto the inner wall of the corresponding receptacle using an energy ray-hardenable adhesive, it is possible to realize the adhesion reaction under equal conditions and to reach a uniform adhesion strength for a plurality of individual pieces of materials, whereby the securing operation can be realized efficiently due to reduction in the hardening reaction duration and, at the same time, the mechanical processing work on the resulting secured material pieces by cutting and/or grinding may be carried out easily due to reliable attainment of a designed definite adhesion strength at normal temperatures. By selecting an adhesive of adequate viscosity, the occurrence of penetration of the adhesive into the adhesive mass can be prevented, whereby denaturation of individual pieces of materials can be excluded.

The apparatus for analyzing individual pieces of materials according to the present invention comprises the above-mentioned apparatus for securing individual pieces of materials and an apparatus for realizing the analysis. For the apparatus for realizing the analysis, there may be employed commonly used ones for analyzing, for example, chemical components or characteristic properties, of materials including those based on spectroscopic analyses, image analyses with image inputting function, Laser Abrasion-ICP mass spectrometric analysis and mass spectrometric analyses. For such an apparatus for realizing the analysis, there may be exemplified those based on spectroscopic analyses, including those using visible lights, infrared rays, ultraviolet rays, fluorescent rays, Raman effect, X-rays and two-dimensional colorimetry; techniques employing numeric computation, such as mass spectroscopic analysis; techniques for image reading devices including MRI, ultrasonic diagnosis units, microscopes (including electron microscope), television and image scanners; and analyses by observation, determination and recording on images produced by means of photographs, as well as visual analysis.

The analysis using the apparatus for analyzing individual pieces of materials according to the present invention is realized for the material pieces secured on the holder of the apparatus for securing individual pieces of materials according to the present invention by analyzing the settled material pieces as such by mounting the holder retaining the secured individual material pieces on the apparatus for realizing the analysis mentioned above. The analysis technique to be employed may be that designated for each contemplated specific purpose. The techniques for preparation and pretreatment of individual pieces of materials may be selected in a proper way for each specific analysis.

For instance, for detecting distribution of a specific chemical component over a lateral sectional area of each seed of a plant, individual seeds are fixedly secured in the receptacles on the holder of the apparatus for securing material pieces according to the present invention at a definite posture, whereupon each seed is processed in the secured state as such by cutting off the tip portion of the endosperm part at the same level with subsequent grinding of the cut face to form the analyzing surface on each of the seeds. For cutting a hard material piece, such as a seed of a plant, it is favorable to employ a solid cutting device, such as a diamond disc used in dental treatment, with which cutting is realized by reciprocal motion of the disc so as to reduce the load applied onto the seed sample, whereupon the cut surface is further processed by grinding up to a depth of from several to about 50 µm to form a smooth analyzing surface. Since the adhesive has completely been hardened, the cut seed maintains its original posture, so that the analyzing surface is formed on each individual seed at once and the same level in planes corresponding to all the secured seeds.

For avoiding denaturation of individual pieces of materials to be analyzed, it is preferable to perform the cutting work while cooling the material pieces using a cooling medium, such as dry ice or liquid nitrogen, at a supercryotic temperature under inert atmosphere. Materials having a higher water content and/or soft consistency can be cut at a high efficiency by solidifying the material by cooling.

For performing spectroscopic analysis of individual pieces of materials, the analyzing surface formed on each individual material piece in the manner as described above is irradiated with an electromagnetic ray, such as infrared rays or so on. The individual material pieces are sustained in an equal definite secured state at a definite posture with respect to the optical axis of the irradiated electromagnetic ray by the use of the adhesive according to the present invention and, therefore, the analyzing surface on each individual material piece is formed with cut plane(s) exactly the same for all the material pieces, so that the analysis can be realized at a high efficiency and in a high accuracy for all the material pieces.

In the case where the occurrence of analysis noise is rather reduced when there is no difference between the incident light and the reflected light as in infrared spectroscopic analysis, the accuracy of the analysis may be increased by the formation of an analysis noise reducing reflective layer, such as a gold layer, by vapor deposition over the surface of the holder on the side onto which the incident light is irradiated, since a reflective layer not causing any influence on the detection of the chemical components of the analyzed material is formed over the reflecting surface.

In the case where the occurrence of analysis noise is rather reduced when the incident light is subjected to a photoabsorption as in a two-dimensional calorimeter, the occurrence of analysis noise is reduced favorably by forming a layer not causing analysis noise, such as a carbon black layer, by vapor deposition on the reflective layer, such as a gold layer, on its side on which the analysis is performed. Alternatively, by coating the surface of the holder on the side, on which the analysis is effected, with a substance not causing analysis noise, analysis of the material to be analyzed can easily be performed by picking up only the data for the material to be analyzed from the detected analysis data by a computation technique, whereby the accuracy of the analysis is increased simultaneously in addition to an attainment of ease of computation.

For performing analysis of a molecular structure over a curved surface, such as the surface of a seed of a plant, it is able to represent the analysis results in the form of a three-dimensional image by having resort to computer operation for correcting the analysis results for the detected strengths for functional groups by determining the distance to each site of the material by, for example, a visible light or an ultrasonic wave.

Alternatively, it is possible to analyze the characteristic features of the morphogenesis of a seed of a plant during the growth thereof at a high accuracy, by processing the seed in a part thereof by cutting along planes of different inclinations, whereupon the analysis is effected on each cut plane of different inclination using an electromagnetic ray having polarization.

When the analyzing surface is ground again after completion of an analysis, a new analysis surface can be formed at a deeper level, whereby a three-dimensional analysis of the material can be realized by repeating such after-grinding with renewed analysis.

For cereal grains and plant seeds, the ratio of starch to bran thereof can be determined using the analysing apparatus according to the present invention in such a manner, that the cereal grains or the plant seeds are crushed into powder and the resulting powder is compacted into grains of equal shape and size, whereupon the analysis procedures described above are carried out for these grains, namely, by securing them in the receptacles on the holder, forming an analysis surface on each of them and performing analysis by a pertinent analysis technique, such as spectrophotometry etc. The analysis can be performed for a transferred layer from a cut face of individual material piece or the compacted grain prepared by transferring the superficial layer of cut face onto any other pertinent surface. The starch/bran ratio can be determined by a spectrophotometric analysis based on the difference in the absorbancy between starch and bran. Also in such a modified analysis technique, an efficient and accurate analysis result can be obtained, since the grains are secured under equal conditions using the adhesive.

For analyzing a flappy thin article, such as a seed coat, spectroscopic analysis can be utilized in such a way, that the thin article is secured on the opening of the receptacle by fixing the periphery thereof on the inner wall of the opening with the adhesive, whereby a spectroscopic analysis by light transmission can be applied thereto. When an extremely thin seed coat which is difficultly fixed steadily has to be analyzed, analysis by the analysis apparatus according to the present invention may successfully be performed by applying a slight tension onto the seed coat by imposing a slight pressure or sucking on the seed coat face, whereby the reproducibility of the analysis results can be increased.

For effecting an analysis by light transmission, such as Laser Abrasion-ICP mass spectrometric analysis, it is preferable to proceed with the procedure in such a manner that each individual material piece is secured on the inner wall of the receptacle so as to face the original cut face of the piece to the hollow space of the receptacle and the rear side part of the piece protruding out from the receptacle is cut off so as to leave a thin disc-like slice of equal thickness having smooth cut faces on the opening of the receptacle, for which the analysis by light transmission is carried out. Here, it is favorable to take a measure of preventing the occurrence of analysis noise due to impingement of the transmitted laser beam onto the holder made of, such as, an acrylic resin by, for example, providing the receptacle at the portion where the laser beam passes through with a vacant gap or with a shielding means, such as Teflon, against the transmitted laser beam. For effecting, for example, infrared spectroscopic analysis of flappy thin articles, it is favorable to secure the article on a hollow receptacle using the adhesive.

The process for analyzing individual pieces of materials may not be limited to the use of the securing apparatus and the analyzing apparatus according to the present invention, but can be realized independently by spectroscopic technique by irradiating an electromagnetic ray, such as an infrared ray, ultraviolet ray or so on, onto the naked surface, onto a cut face or onto a transferred layer of the individual material piece. For providing each individual material piece with a cut face, the material piece may be cut along a horizontal and/or any other inclined plane or along a curved face. When preparing the analyzing surface on the material piece under the combination of cut faces mentioned above, a three-dimensional analysis of the material piece can be realized. By a spectroscopic analysis, the sorting accuracy can be increased when the incident and/or reflected light is subjected to polarization, whereby analysis concerning the molecular structure can be realized, by the output lights having different phases.

The apparatus for sorting individual pieces of materials according to the present invention is composed of the above-mentioned securing apparatus, the above-mentioned analyzing apparatus and a sorting device operative to sort individual material pieces. Here, the sorting device is constructed so as to sort individual material pieces by dispensing the individual material pieces into groups having designated features with respect to, for example, composition of the constituting components, characteristic properties and so on, based on the results of the analyses obtained in the analyzing apparatus. Such sorting may be realized by, for example, securing individual pieces of materials, such as plant seeds, on the securing apparatus and performing the analysis with or without cutting a portion of the individual material piece, whereupon the material pieces indicated by the analysis to have favorable features are separated or grouped. The sorting operation may be effected by means of, for example, a dispenser rod operative to push each material piece out from the receptacle.

By the process for sorting individual pieces of materials according to the present invention, it is able to obtain sorted products through the process steps of securing a plurality of individual pieces of materials in the receptacles of the securing apparatus, analyzing each individual material piece on the analyzing apparatus and sorting each individual material piece based on the analysis results obtained in the analyzing apparatus with respect to each specific characteristic feature, such as the composition of the constituent components, the characteristic properties of the material piece or so on, to obtain sorted products. The analysis results may be obtained in a form of numerical data for, for instance, absorbancy or the like, in spectral curves and/or in two dimensional images. The sorting may be effected into groups, such as two groups, for example, passed and rejected groups, three groups, for example, superior, medium and inferior groups, or even more numbers of groups. For organic materials, the resulting data as to, for example, the degree of unsaturation of lipids, molecular structures, such as $\alpha$-helix, $\beta$-sheet and so on, distribution of trace metals in enzymes etc. in tissues of an organism, may be utilized for discrimination of individuals, for judgement of the district of the production origin, for assessment of material quality, for pathological diagnosis and for others, as data to be transmitted by being labelled on the material piece or through an information transmission means. Sorting can also be realized at a high efficiency and a high accuracy, since the analysis can be attained at a high efficiency and high accuracy. By entering a plurality of such data in, for example, a hologram to utilize it as a quality information of materials to contribute to quality verification, recognition of the district of production origin and so on.

The resulting sorted products may be utilized not only as such but also with further processing by multiplication and/or amplification thereof. For instance, seeds of a plant can be processed by multiplication for effecting elaborate sorting of higher quality descendants. Sorted products may be obtained with multiplication and/or amplification by means of other techniques, such as cloning and so on.

As described above, the present invention can provide an apparatus and a process for effecting securing of individual pieces of materials, the apparatus comprising an energy ray-permeable holder provided with a plurality of receptacles adapted for receiving each individual material piece in a definite arrangement and a definite posture with an energy ray-hardenable adhesive placed in the interspaces between each individual material piece and inner wall of the corresponding receptacle, wherein each individual material piece is bonded and fixedly secured in the receptacle at a definite posture by the process for effecting securing of individual pieces of materials under equal conditions of hardening of the adhesive at normal temperatures with equalized hardening duration and adhesion strength, whereby the resulting secured individual material pieces can be processed in a steady and reliable way without suffering from denaturation of the material to form an equal analyzing surface on each individual material piece to be used for effecting the analysis, whereby the processed individual material pieces can be used for the examination steps of analysis and sorting at a high efficiency and a high accuracy.

According to the present invention, an apparatus and a process for effecting analysis of individual pieces of materials are provided, which can afford analysis of each individual material piece at a high efficiency and a high accuracy under a reduced computer processing load by attaining a reduction of the occurrence of analysis noise by the employment of the apparatus and the process for securing individual pieces of materials according to the present invention described above to thereby attain restriction of the area of analysis site.

It is possible according to the present invention to obtain a plurality of analysis data from one and the same material piece by subjecting the material pieces secured on the securing apparatus according to the present invention as such to analysis in the analyzing apparatus according to the present invention by a non-destructive analysis technique, such as two-dimensional calorimeter, infrared spectrometer or so on, and subsequently by a penetrable analysis technique, such as using dyeing with a reactive reagent, irradiation with a laser beam or so on, in the same apparatus.

It is further possible to obtain three-dimensionally expressed computation information by repeating similar analysis procedures on each renewed analyzing surface prepared by subjecting the original analyzing surface to renewed grinding and to repeated processing works by the procedures for forming the analyzing surface in succession.

According to the present invention, it is able to provide an apparatus and a process for sorting individual pieces of materials under utilization of the apparatus and a process for securing individual pieces of materials and the apparatus and a process for analyzing individual pieces of materials according to the present invention described above with further incorporation of a sorting device for sorting each individual material piece based on the results of the analyses obtained by the process for analyzing individual pieces of materials according to the present invention, whereby individual pieces of materials exhibiting designated specific characteristic properties can be sorted at a high efficiency and a high accuracy.

The sorted product according to the present invention is obtained by the sorting technique according to the present invention at a high efficiency and a high accuracy and can be utilized for realizing efficient multiplication and/or amplification of prospective descendants of individual pieces of materials.

THE BEST MODE FOR EMBODYING THE INVENTION

Below, the present invention will further be described in more detail by way of EXAMPLES with reference to appended drawings and computer-processed images obtained for seeds of a plant (wheat). For the analysis by infrared spectroscopy, details will be described with respect to the corresponding drawings.

An embodiment of the apparatus for securing individual pieces of materials according to the present invention is shown in FIGS. 1a and 1b, both in a perspective view, wherein FIG. 1a illustrates the apparatus in an off-duty state and FIG. 1b illustrates an on-duty state.

FIGS. 2a to 2d illustrate the course of processing of seeds of wheat by the technique according to the present invention, each in vertical sectional view.

In the embodiments of the apparatus shown in FIGS. 1a, 1b and 2a to 2d, the holder 1 comprises, all integrally molded, a stage 2 composed of a flat top panel 2a extending in a horizontal plane and two supporting side webs 2b arranged at both side ends of the panel protruding down for supporting the holder. The top panel 2a is provided on its upper surface with a reflective layer 3 made of a gold coating formed by vapor deposition. In the top panel 2a, a plurality of receptacles 4 in a form of cut off openings are formed in several rows. The receptacles are in fact distributed over the entire extent of the top panel 2a, though not shown in the Figs.

Figure 2A:
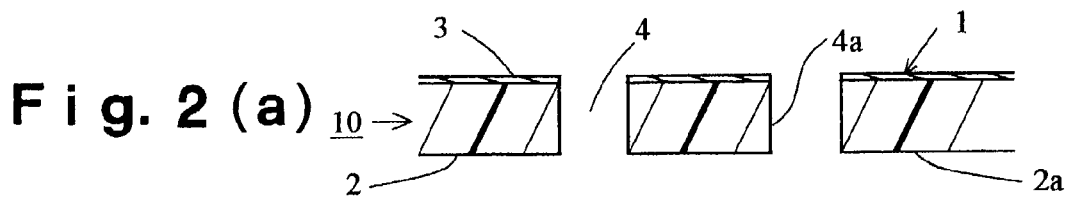
FIGS. 2a, 2b, 2c and 2d are explanatory illustrations explaining the course of an exemplary processing of seeds of a plant using an apparatus according to the present invention by showing the state of the sample holder at different processing stages, each in a sectional view.
Figure 2B:
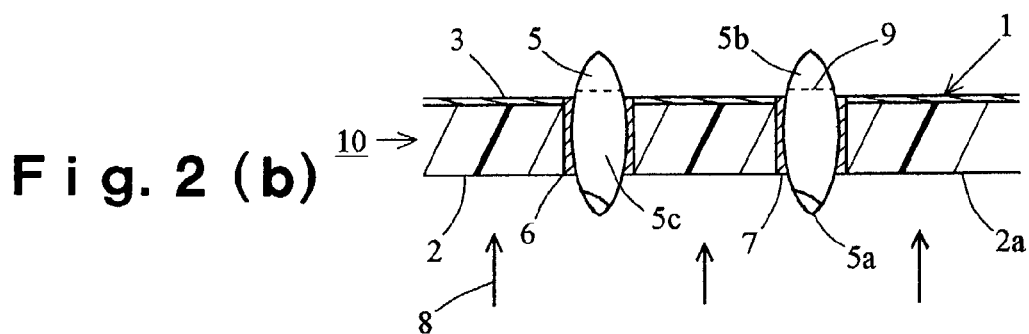

The apparatus 10 for securing individual pieces of materials is constructed in such a manner that, as shown in FIG. 2b, individual pieces 5 of material, here, seeds of wheat, are each received in a receptacle 4 of the holder 1 in an equal posture with their embryo side being at the lower side, wherein the interspaces 6 between each seed and the inner wall face of the corresponding receptacle are filled with an energy ray-hardenable adhesive 7, here, a light-hardenable adhesive, whereby the wheat seed 5 is fixedly secured in the receptacle 4 by hardening of the adhesive 7 by irradiation of a light. The receptacles 4 each may have a size of 3–6 mm, preferably 3.5–5 mm, in diameter for the holder assigned for dealing with wheat seeds.

The practical procedure for securing individual pieces of materials using the apparatus for securing individual material pieces described above is as given in the following: Thus, starting from the original off-duty state as shown in FIG. 1a and in FIG. 2a, each wheat seed 5 is received in the receptacle 4 in a posture with its lower end being the side of embryo 5a and the top end on the reverse side, namely, the side of endosperm 5b protrudes from the receptacle 4, as shown in FIG. 2b. The interspaces between the wheat seed 5 and inner wall 4a of the receptacle are filled with the adhesive 7, whereupon the so-filled adhesive is irradiated with an energy ray (light ray) 8 from the side devoid of any reflective layer 3 of the stage 2, whereby the hardening reaction is initiated in the mass of adhesive 7 in the portion where it is irradiated with the light ray 8 and in the portion where it is irradiated with the light ray reflected by the reflective layer 3 to cause it to harden.

The hardening reaction starts by irradiation of the light ray 8, so that each mass of the adhesive 7 in different receptacles 4 is caused to initiate the hardening reaction at the same point in time as the commencement of light irradiation under the same condition, nothwithstanding that each receptacle was filled with the adhesive at different points in time. In this manner, each mass of adhesive 7 can attain an equal but high adhesion strength within a brief time. The resulting fixedly secured wheat seeds are then subjected to mechanical processing by cutting off each end portion 5b not essential for their growth by several reciprocal motions of a cutter (not shown), such as a diamond disc or the like, so as not to generate superfluous frictional heat and stress upon the cutting work, with subsequent grinding of the resulting cut face to a slight depth to build up a final smooth analyzing surface 9 for serving for the analysis thereon. FIG. 1b illustrates the secured state of the seeds 5 at this moment. The adhesive mass has been hardened before this moment and, therefore, there occurs no change in the posture of the seeds 5 by the cutting work, whereby every analyzing surface can be formed on one and the same plane.

Figure 2C:
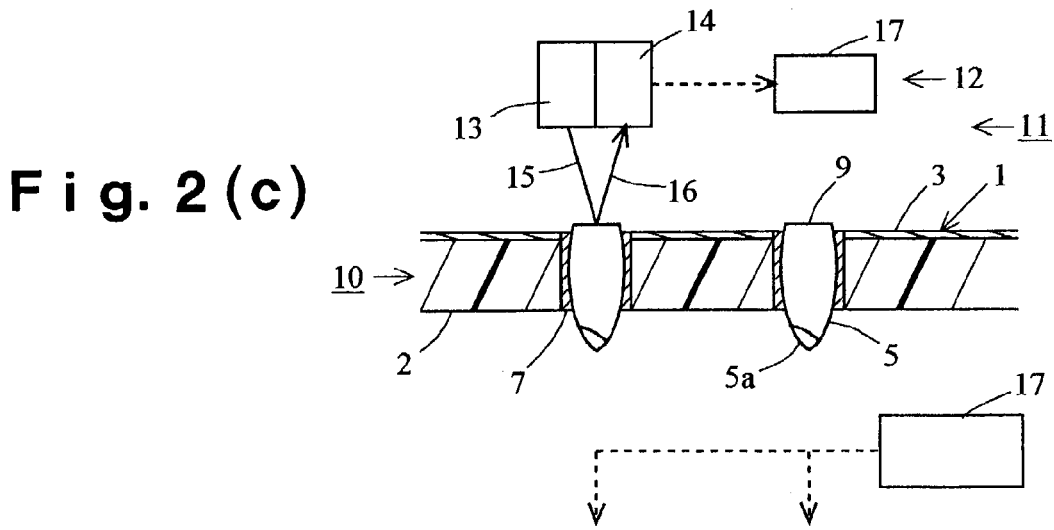

FIG. 2c illustrates roughly the apparatus 11 for analyzing individual pieces of materials according to the present invention which is constructed such that the holder 10 having secured thereon the individual pieces 5 of materials is mounted together with the material pieces 5 as such on an analyzing device 12, whereupon the analysis is performed for the individual material pieces on the holder successively. The analyzing device 12 comprises a light irradiating system 13 and a light receiving system 14 for an infrared ray, in which an infrared ray 15 is irradiated from the light irradiating system 13 onto the analyzing surface 9 of the material piece 5 and the reflected ray 16 from the analyzing surface is detected by the light receiving system 14 to effect the analysis, wherein the resulting analysis signals are inputted to a computer processing control unit 17 where they are recorded.

The individual material pieces are analyzed in such a way that the holder 10 having fixedly secured thereon the material pieces is mounted on the analyzing device 12, in which individual material pieces held on the holder 10 are analyzed successively in accordance with the control signals passed from the computer processing control unit 17. The analysis may be performed in such a way that the infrared ray 15 is irradiated from the light irradiating system 13 of the analyzing device 12 onto the analyzing surface 9 of each individual material piece 5 and the reflected ray 16 from the analyzing surface 9 is detected by the light receiving system 14, to thereby attain analysis of the distribution of the composition of the constituent components, characteristic features and so on over the analyzing surface 9. By scanning the analyzing surface by the irradiated ray 15, analysis data over the entire analyzing surface can be obtained. The results of the analyses are taken out and recorded in the computer processing control unit 17 in a form of digital information or two-dimensional images.

Figure 2D:
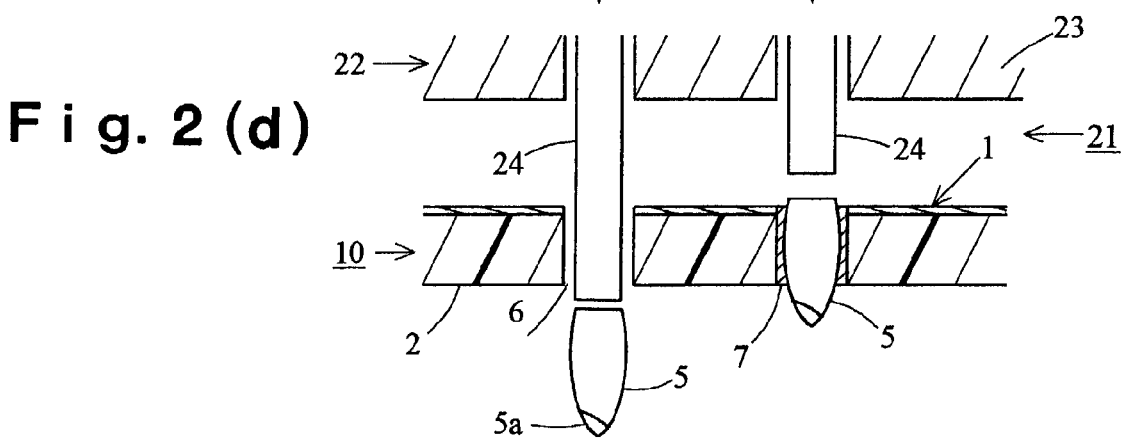

FIG. 2*d* is an explanatory illustration of the apparatus 21 for sorting individual pieces 5 of materials according to the present invention, in which the holder 10 having individual material pieces which have been subjected to the analysis is transferred to a sorting device 22 in which they are sorted in accordance with the control signals delivered from the computer processing control unit 17. The sorting device 22 is constructed such that a plurality of dispenser rods 24 are each arranged in a shed board 23 in a position corresponding to each corresponding receptacle 4 for the material piece 5 so as to push out the material piece judged by the analysis to be rated from the receptacle 4 in order to dispense it into a collector means (not shown).

Individual pieces of materials 5 are sorted by the apparatus 21 for sorting individual pieces of materials according to the present invention in such a way that the holder 10 having thereon the secured individual material pieces which have been subjected to the analysis is transferred from the analyzing unit 12 to the sorting device 22, whereupon the material piece 5 judged by the analysis to be rated is pushed out of the receptacle 4 by operating the dispenser rod 24 corresponding to the material piece 5 in accordance with the control signals delivered from the computer processing control unit 17 to dispense it into a collector means (not shown). The material piece 5 sorted in this manner can be used directly for multiplication as such, since it contains the living embryo 5*a* in an intact state, whereby multiplication of elaborately selected individual can be multiplicated which will contribute to a wide distribution of descendants of superior strain. While a recessive heredity leading to the occurrence of rejects should also be expected to accord to Mendel's laws, it is able to increase the sorting accuracy for sorting genuine strains by repeating such sorting procedures many times. The material pieces which are judged as rejects can be removed by operating corresponding dispenser rods 24 from the holder 10.

The operation for pushing individual pieces of materials out of the receptacles can be made easy by employing an adhesive exhibiting lower penetrability into individual material pieces, since thereby bonding of individual material pieces onto the inner wall of the receptacle is realized only between a more thinner superficial layer of the material piece and the wall surface of the receptacle. In particular, for sorting cereal grains, multiplication can be attained more easily, since the bonding of the grain onto the receptacle wall can be effected only between the hull of the grain and the wall surface, whereby the seed can be taken out in intact state. Especially, it is preferable to secure each seed in the receptacle with the side of its embryo 5*a* protruding from the receptacle 4, as shown in FIGS. 2*b*–2*d*, since thereby the embryo 5*a* is not affected by the procedures of securing, analysis and sorting. Thus, sorting of individual pieces of materials can be realized in such a manner that the analysis results are reflected to the sorting without any modification.

Figure 3:
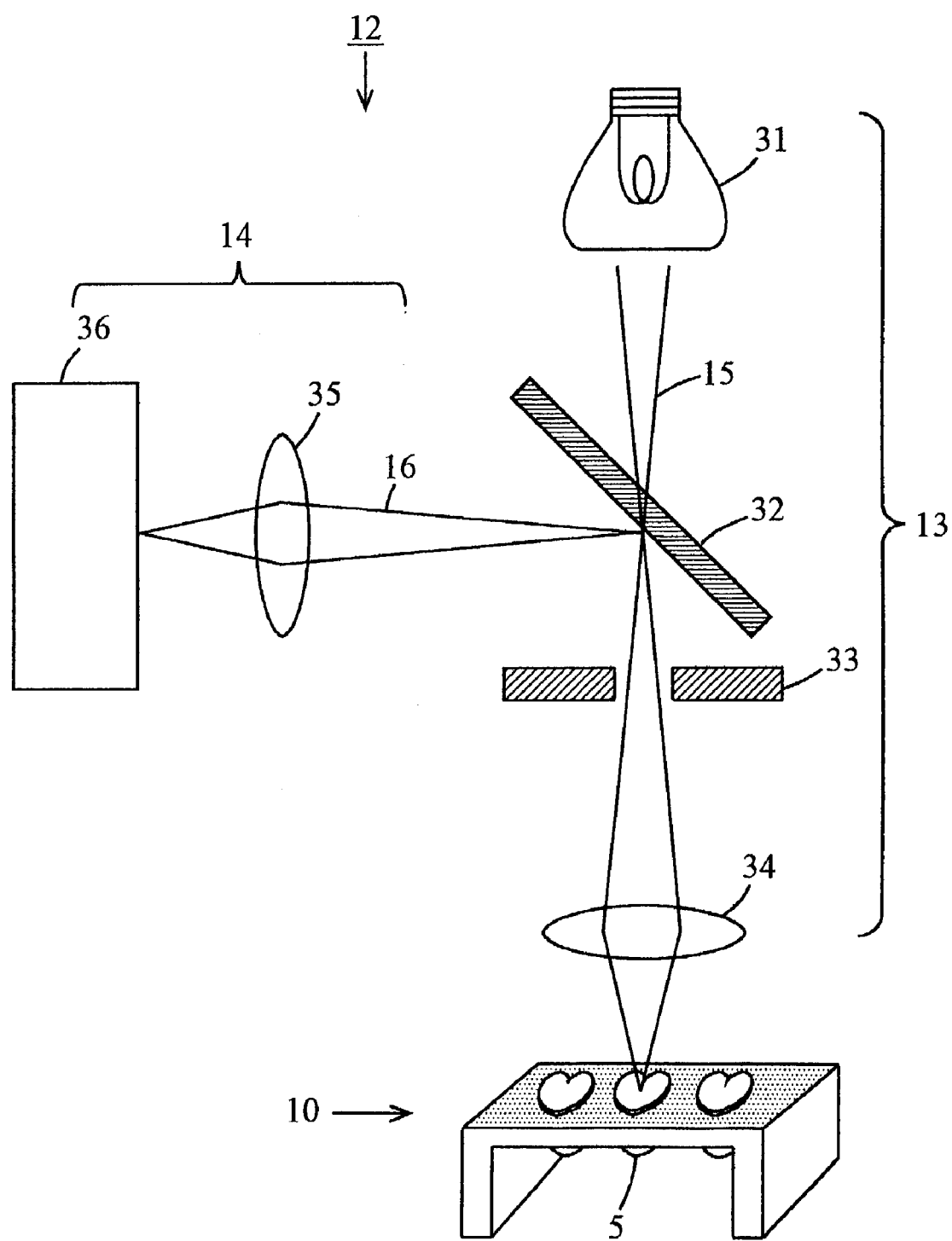
FIG. 3 is an explanatory illustration of an embodiment of the apparatus for analyzing individual pieces of materials according to the present invention showing the light paths for spectroscopically analyzing individual pieces of materials.

FIG. 3 shows one embodiment of the apparatus 11 for analyzing individual pieces of materials according to the present invention indicating the light paths. Here, the analyzing unit 12 comprises, as the light irradiating system, a light source 31, a half mirror 32, a diaphragm 33 and an objective lens (or mirror) 34 and, as the light receiving system 14, a converging lens (or mirror) 35 for converging the light from the half mirror 32 and a detector 36. The apparatus 10 for securing individual pieces of materials is arranged in opposition to the objective lens.

In the above apparatus 11 for analyzing individual pieces of materials according to the present invention, the apparatus 10 for securing individual pieces of materials is disposed opposite to the objective lens 34 of the irradiating system 13 of the analyzing unit 12, wherein the analyzing surface 9 of each individual material piece 5 secured on the material piece securing apparatus 10 is irradiated with the irradiating light 15 from the light source 31 via the half mirror 32, the diaphragm 33 and the objective lens 34. The reflected light 16 from the analyzing surface 9 is guided via the objective lens 34 and the diaphragm 33 and reflected again by the half mirror 32 and is converged through the converging lens 35, before it is detected by the detector 36. If a detecting device allowing two-dimensional detection of, for example, distribution of a chemical component over the analyzing surface 9 and capable of displaying the detected signals on a display, such as a line array detector, is used as the detector 36, the results of the analysis can be displayed as a two-dimensional image.

By the above-described mode embodying the present invention, in which the material piece is secured in the receptacle 4 of the securing apparatus 10 using an energy ray-hardenable adhesive, not only can an equalized hardening condition can be attained but also the processing work for forming the analyzing surface on each material piece can be effected without suffering from the occurrence of denaturation of the material piece due to an attainment of the reduction of the hardening time and increase in the adhesion strength, thus permitting formation of the analyzing surface on each individual material piece on the same plane without causing any alteration of the posture of the material piece by the cutting work imposed on each material piece, whereby an efficient and highly accurate analysis can be performed. By sorting each individual material piece based on the results of such accurate analyses, an accurate and efficient sorting of individual pieces of materials can be realized.

FIGS. 4*a*, 4*b* and 4*c* each illustrate a further embodiment of the apparatus for securing individual pieces of materials according to the present invention in a perspective view. In these embodiments, the holder 1 is provided with a plurality of receptacles 4 formed in the stage 2 in a protruding portion 2*d* on both sides thereof in two rows so as to each receive a material piece 5 in a posture in which one end of the material piece is retained on the base panel 2*c* and a part of each material piece is held inserted in each receptacle 4 with the interspaces between the material piece and the inner wall of the receptacle being filled with an adhesive 7. Each individual material piece 5 is secured fixedly in the receptacle 4 by causing the adhesive 7 to harden. Such a holder 1 permits easy positioning of the material pieces 5 in the receptacle 4. In the embodiment of FIG. 4*c*, the end portion of the material piece, i.e. wheat seed, including the embryo 5*a* is fixed on a fitting plate 20 using a fixing means 19. This embodiment allows easy handling of the so-fixed row of seeds by cutting the row of fixed seeds off from the holder to be used for the multiplication of the seeds with easy recognition of correspondence with the analysis results of corresponding seeds.

Figure 5:
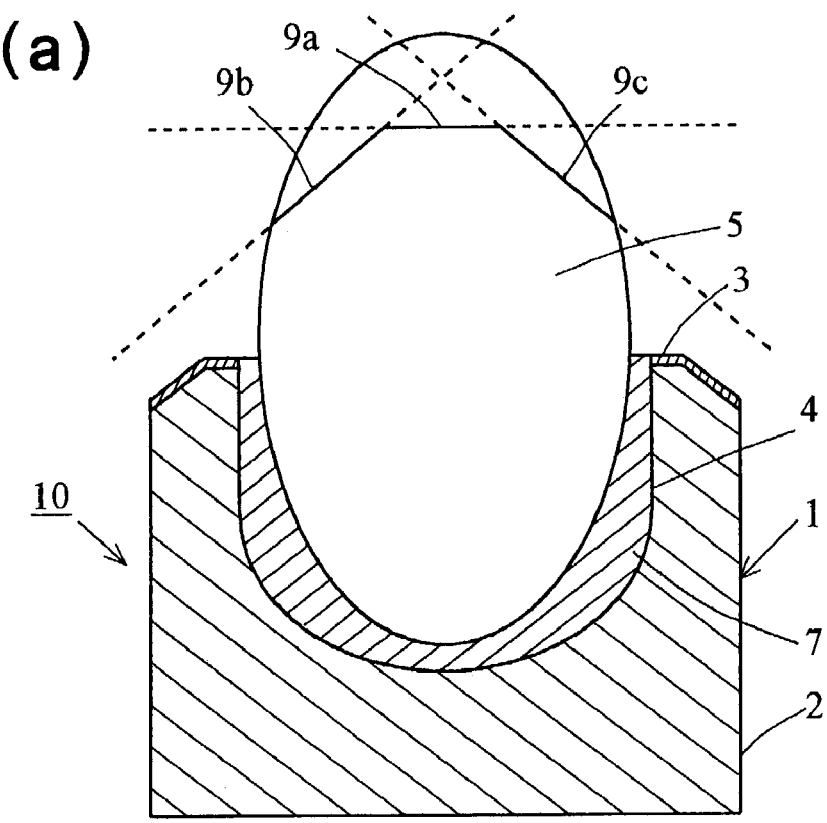
FIGS. 5a and 5b show an inventive example of a material piece received in a receptacle, having formed thereon an analyzing surface consisting of five cut planes, in a vertical sectional view and in a plan view, respectively.
Figure 5:
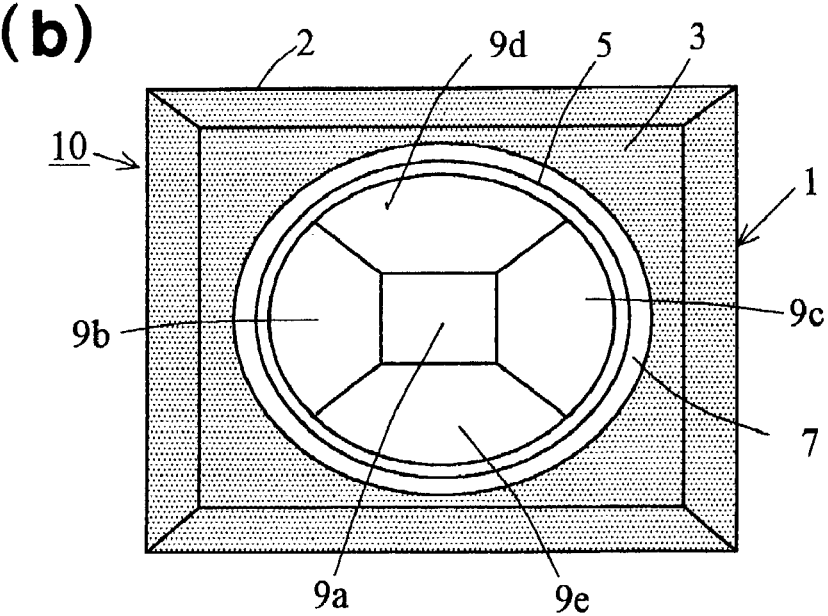

FIGS. 5a and 5b illustrate a further embodiment of the apparatus for securing individual pieces of materials according to the present invention in a vertical sectional view and in a plan view, respectively. This embodiment of the material pieces securing apparatus 10 allows a three-dimensional analysis of each individual material place 5 by preparing the analyzing surface 9 composed of a horizontal face 9a and inclined faces 9b–9e. Here, only one receptacle 4 of the securing apparatus 10 is shown, though a number of such receptacles, may be arranged.

Figure 6:
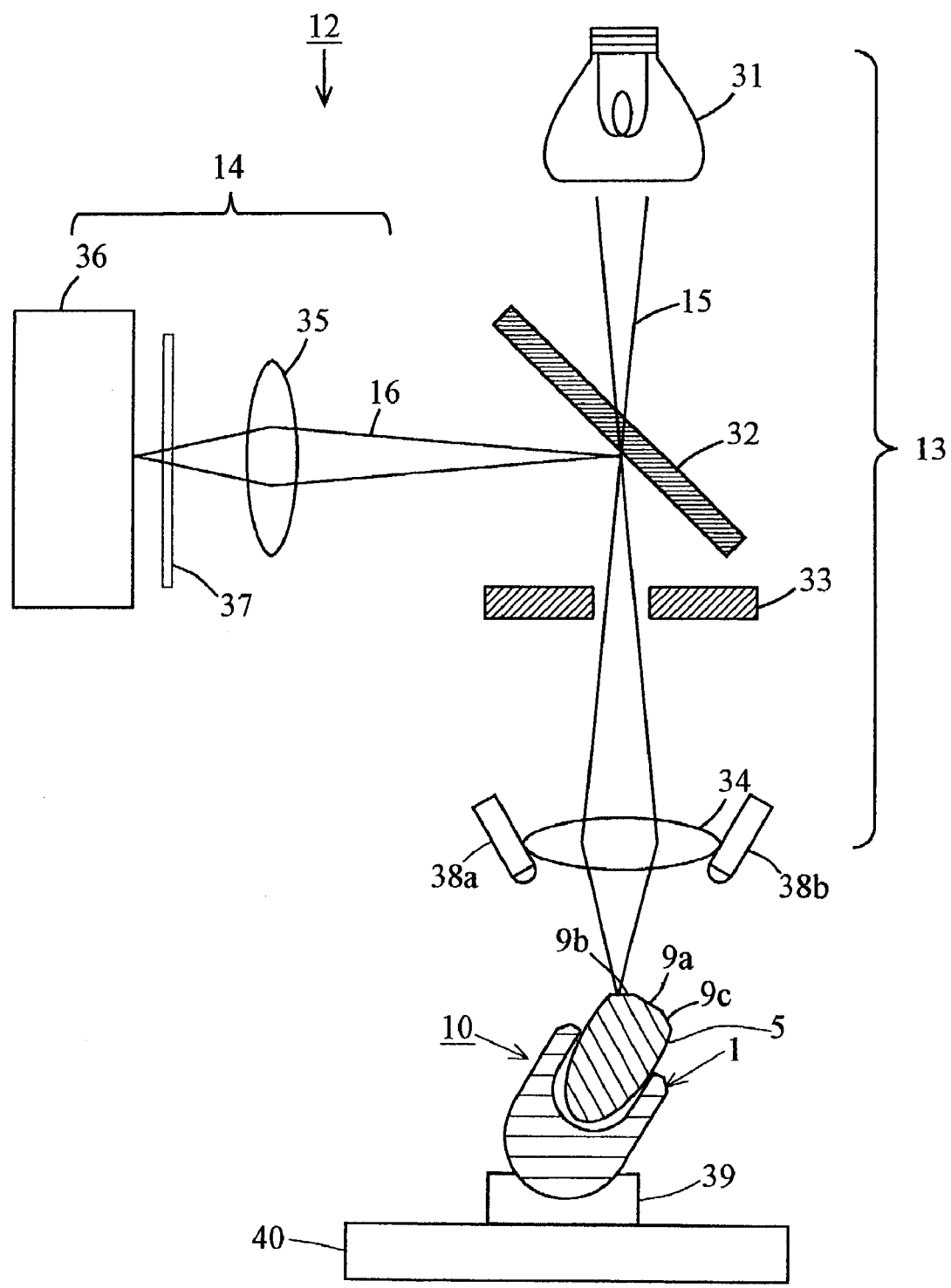
FIG. 6 is an explanatory illustration of another embodiment of the apparatus according to the present invention showing the light paths for spectroscopically analyzing individual pieces of materials.

FIG. 6 is an explanatory illustration of another embodiment of the apparatus for analyzing individual pieces of materials using the holder shown in FIGS. 5a and 5b, illustrating the light paths. The embodiment of the apparatus shown in FIG. 6 comprises a polarizing filter 37 and an autofocusing arrangement 38a, 38b as well as an angle adjusting device 39 and an elevation adjusting device 40 for adjusting each specific analyzing face to be analyzed 9a–9d at a proper analysis position by adjusting the position and posture of the holder 10 by operating the angle adjusting device and the elevation adjusting device. In this embodiment of the analyzing apparatus, the analysis is performed after each specific face 9a–9d of the analyzing surface to be analyzed has been secured at the proper analysis position and the focusing of the optical system has been established by the autofocusing arrangement. By varying the phase of the incident light beam by the polarizing filter 37, it is possible to analyze the object for its chemical composition, molecular weight and molecular structure isolatedly.

FIGS. 7a and 7b show another embodiment of the apparatus 10 for securing individual pieces of materials in a vertical sectional view and in a plan view, before and after the formation of the analyzing surface, respectively. The holder 1 is constructed such that the receptacle 4 is formed in the stage 2 thereof in which the material piece 5 is received in such a manner that the piece 5 is partly inserted therein and fixed by hardening the adhesive 7 filled in the interspaces therein, whereupon the so-secured material piece is processed by cutting the piece along a plane 9g to form the analyzing surface 9a, on which the analysis is carried out by a reflected light. The top surface of the panel 2a of the stage 2 is coated by a reflective layer 3 made of a vapor-deposited gold coating so as to facilitate the hardening of the adhesive 7. On the reflective layer 3, there is provided a noise depletion layer 18 for preventing the occurrence of analysis noise.

FIGS. 8a and 8b show a further embodiment of the apparatus for secured individual pieces of materials according to the present invention in a vertical sectional view and in a plan view, before and after the formation of the analyzing surface, respectively. Here, the holder 1 is constructed such that the receptacle 4 is formed in the stage 2 and the material piece 5 is received therein in such a manner that a part of the material piece 5 is inserted in the receptacle and fixed by hardening the adhesive 7 filled in the interspaces therein, whereupon the so-secured material piece is processed by cutting the piece along a plane 9g to form an analyzing slice 9h, on which the analysis is carried out by a transmitted light.

Figure 9:
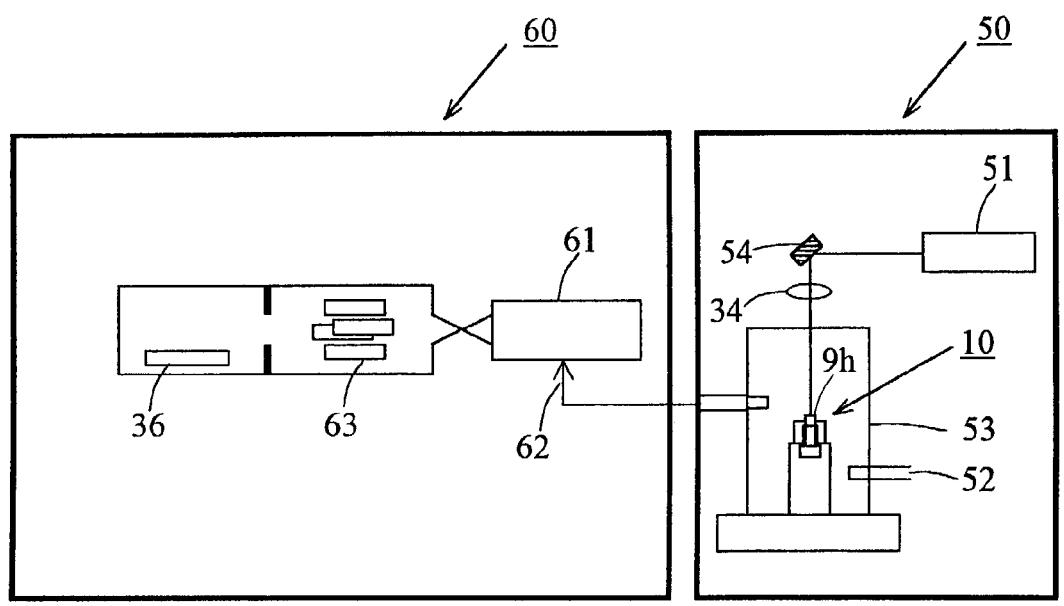
FIG. 9 is an explanatory diagram showing the construction of an embodiment of the apparatus for analyzing individual pieces of materials according to the present invention.

FIG. 9 shows an embodiment of the apparatus for analyzing individual pieces of materials with respect to trace mineral elements, which is composed of a laser abrasion unit 50 and an ICP mass spectrometer 60. This embodiment comprises a laser generator 51, an inlet for argon gas 52, a laser abrasion compartment 53, a mirror 54, a plasma torch 61, a micronized sample inlet 62 and a quadrupole 63. In this analyzing apparatus, a sample 9h to be analyzed constituted of a slice of a seed of wheat secured on the securing apparatus 10, is exposed to a laser beam to produce a micronized disintegrated analysis sample to be carried by a carrier gas and is guided into the plasma torch 61 of the ICP mass spectrometer 60 to cause decomposition of the sample and the decomposition product is caused to pass through the quadrupole 63 to subject it to mass spectrometric analysis of its mineral components under detection by the detector 36.

Figure 4:
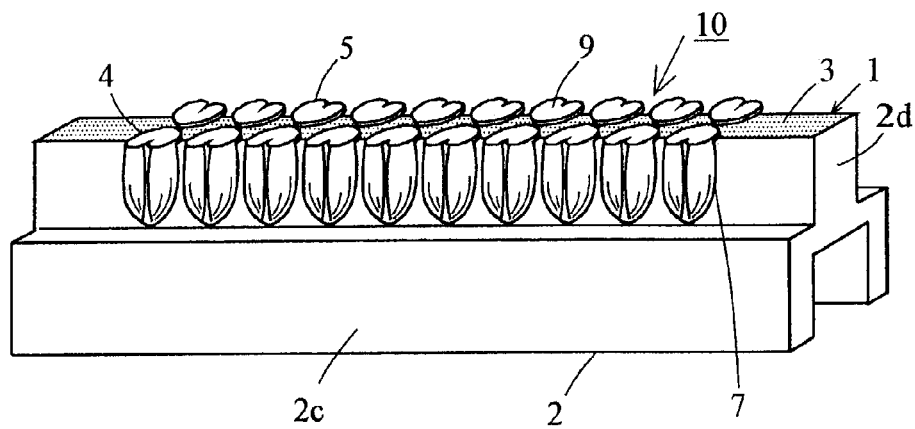
FIGS. 4a, 4b and 4c each show an explanatory illustration of the sample holder for different embodiments, each in a perspective view.
Figure 4:
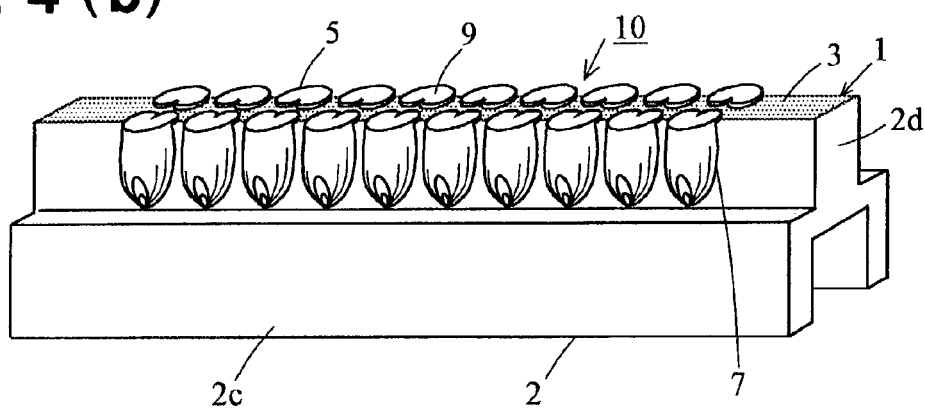
Figure 4:
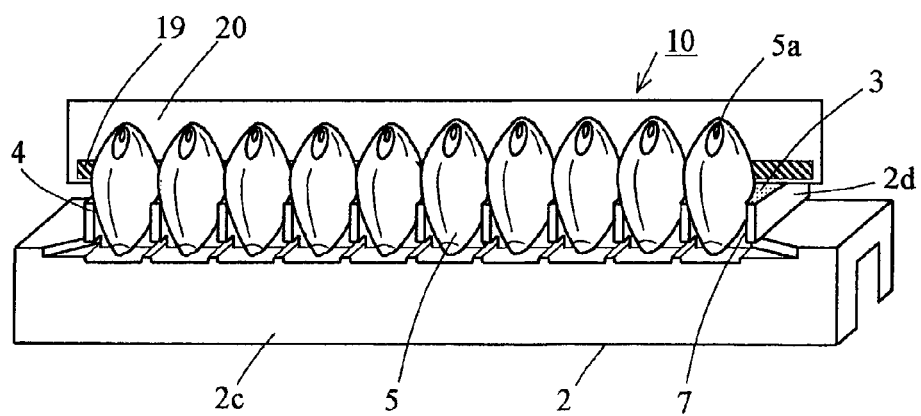
Figure 10:
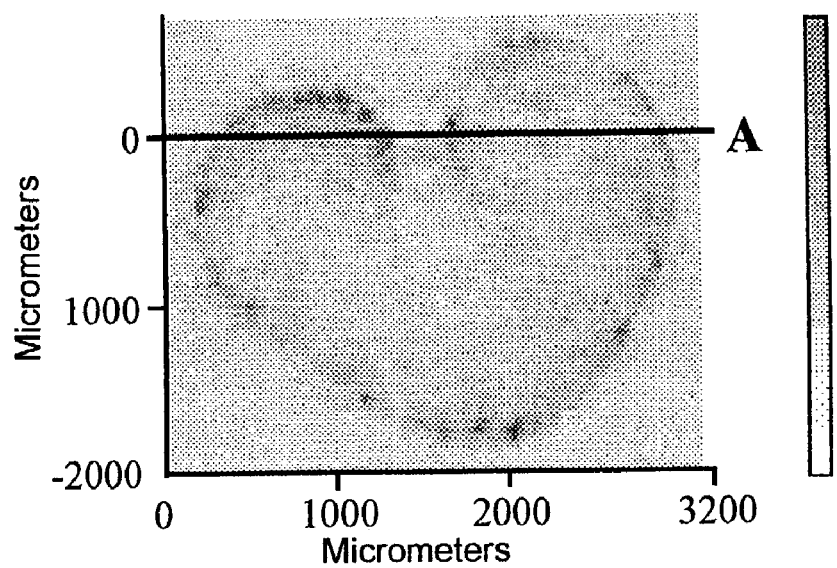
FIGS. 10a and 10b represent the results of an example of an analysis of an analyzing surface of a plant seed shown by a computer-processed image of a section of the seed with respect to a specific chemical component and a linear distribution curve along a line thereof, respectively.
Figure 10:
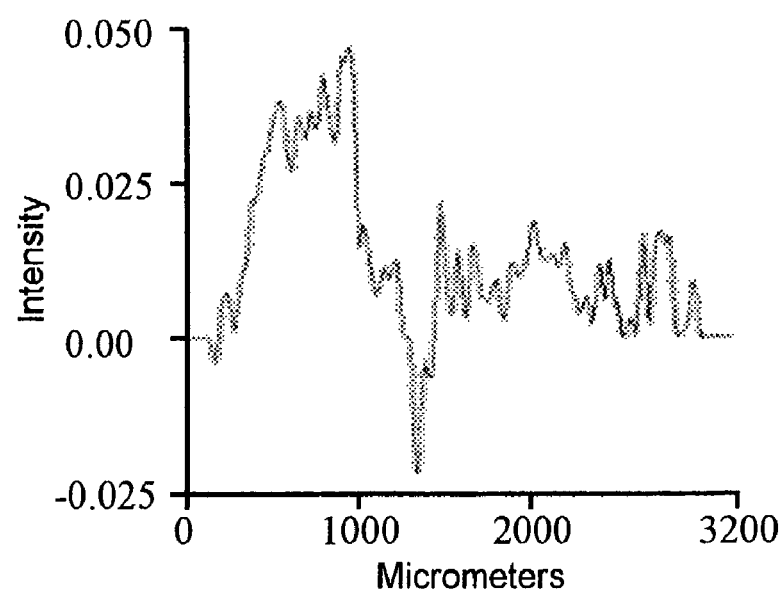

FIGS. 10a and 10b show an example of analysis results obtained using the apparatus shown in FIGS. 3 and 4, in which a seed of wheat was analyzed for the content distribution of amide I which is used as a parameter of protein content, in order to sort a high protein strain of wheat, wherein FIG. 10a is a chemical image showing the distribution of the concentration of amide I over the analyzing surface formed through the endosperm and FIG. 10b shows a linear distribution curve across the analyzing surface along a line for a horizontal portion of a cut face of the endosperm part of the seed obtained by infrared spectrometry. These Figs. show the results of the analysis of a protein in a sample of a wheat strain "Ayahikari", in which it is seen that the protein content is concentrated at specific sites near the hull of the seed.

Figure 7:
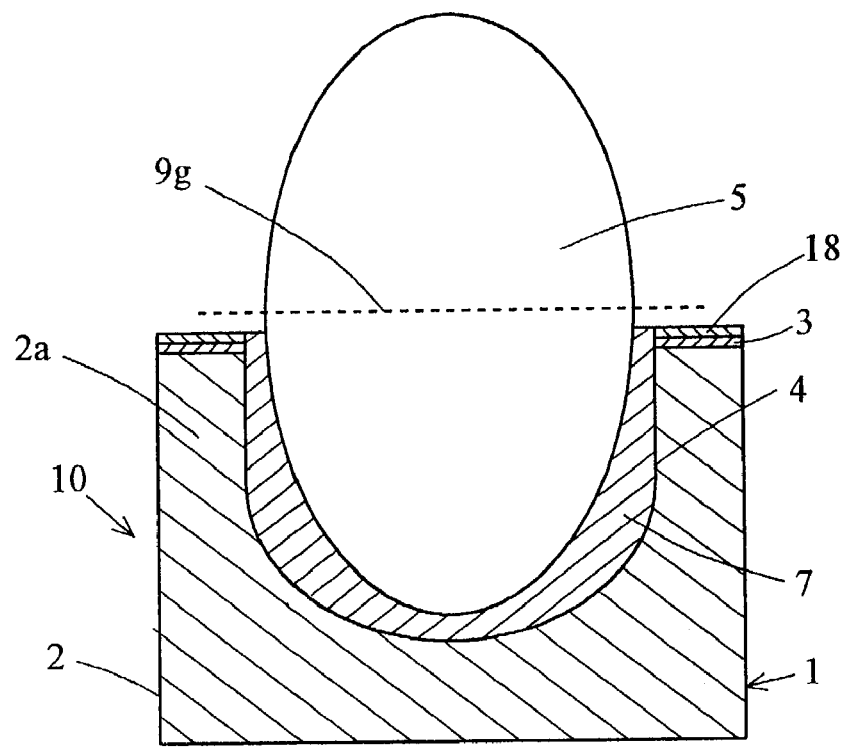
FIGS. 7a and 7b show another inventive example of a material piece received in a receptacle, in a vertical sectional view and in a plan view, before and after a cross-cut analyzing surface is formed thereon, respectively.
Figure 7:
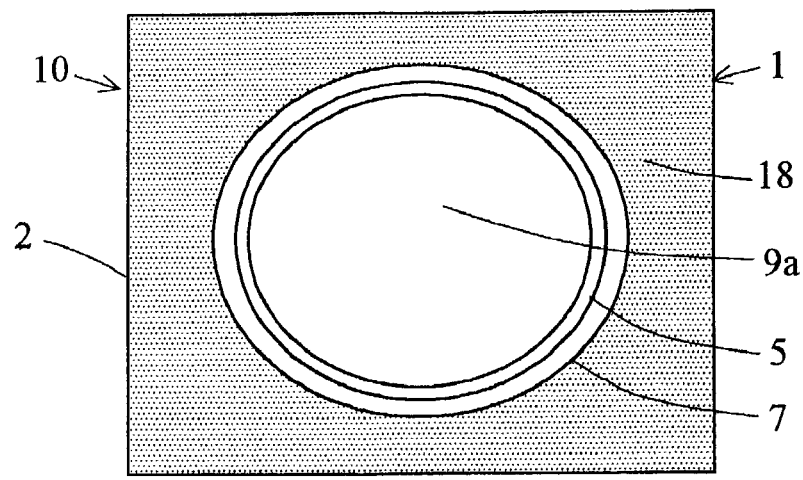

FIGS. 11a–11c show the results of the analyses of seeds of a strain of wheat "Bandowase" by a two-dimensional calorimetric observation performed in order to sort seeds having a higher lightness endosperm by a two-dimensional calorimeter using the analyzing apparatus shown in FIG. 3 employing the securing apparatus shown in FIG. 7. FIG. 11a shows an enlarged imaged distribution of lightness (L*) across the endosperm of a seed of "Bandowase". FIG. 11b is a graph showing L* distribution over the analyzing surface formed across the endosperm in three horizontal planes at different vertical levels. FIG. 11c is a graph showing L* distribution over the analyzing surface formed across the endosperm in three different vertical planes.

FIG. 11d shows an imaged distribution of lightness (L*) over each analyzing surface formed in the endosperm of each of seed specimens of wheat arranged on five (a to e) isolated securing apparatuses 10 encased in a frame. The analysis was performed for each analyzing surface by a two-dimensional colorimeter. The stage 2 of the holder is provided over its top face with a reflective layer of gold which is further coated with a carbon black coating to prevent the occurrence of analysis noise. Due to the prevention of the occurrence of analysis noise, the lightness was able to be determined reliably and the specimens marked by "A" and "B" in FIG. 11d of a strain "Norin No. 61" which exhibited higher lightness values were found to have lightness values of L*=67.13 for "A" and L*=73.99 for "B", respectively. After completion of the analysis by the two-dimensional colorimeter, the specimens can be subjected to further analyses of, for example, the content of crude protein, the amylose/amylopectin ratio and content of lipids, by coating the analyzing surface with ninhydrin solution, iodine/potassium iodide solution or a fluorescent probe.

Figure 8:
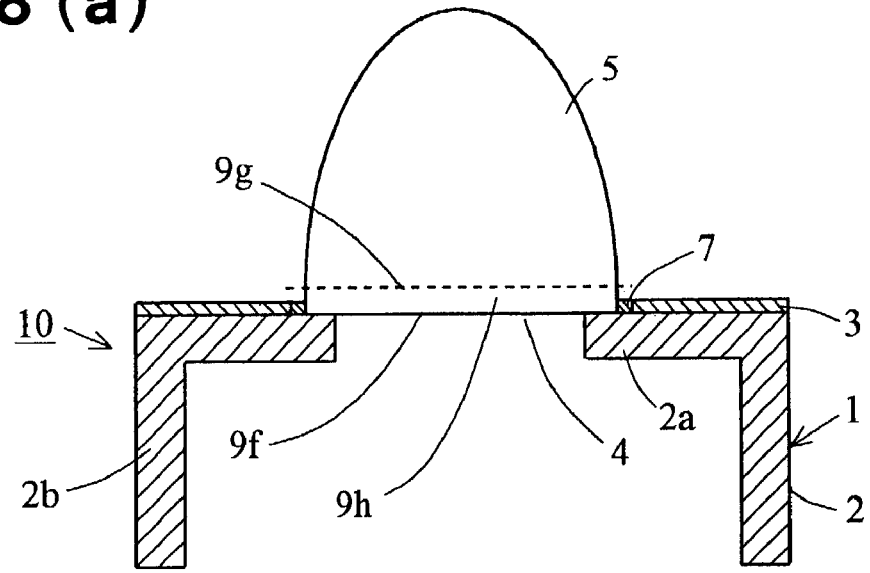
FIGS. 8a and 8b show a further inventive example of a material piece received in a receptacle of another type, in a vertical sectional view and in a plan view, before and after a cross-cut analyzing surface is formed thereon, respectively.
Figure 8:
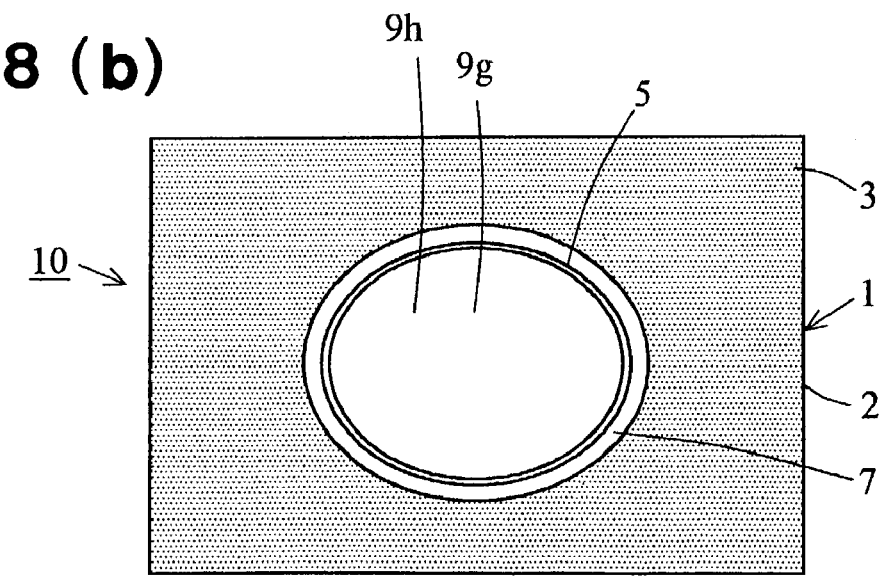
Figure 12:
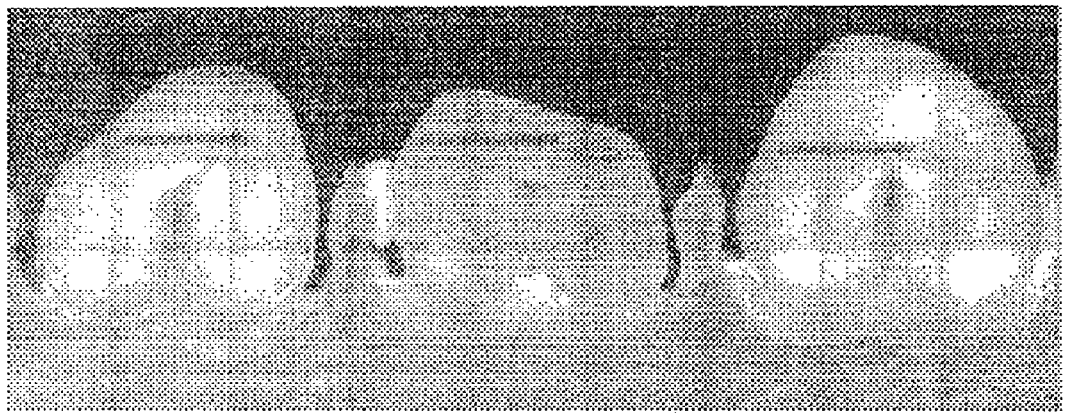
FIG. 12 is a photograph of sliced specimens of wheat seeds secured in receptacles formed in a horizontal panel, taken after having been subjected to laser abrasion-ICP mass spectrometric analysis, showing laser beam scanned marks on the specimen.

FIG. 12 is a photograph of a wheat seed slice specimen of a thickness of 1 mm, after having been analyzed by laser abrasion-ICP mass spectrometric analysis for mineral content distribution over the specimen surface for inspection for heavy metal pollution by, for example, cadmium and so on, using a securing apparatus as shown in FIG. 8 and an analyzing apparatus as shown in FIG. 9. By determining the content of heavy metals by having resort to an internal standard method, a content of cadmium in the range of 0.02–0.03 ppm, a content of arsenic in the range of 0.5–4.9 ppm, a content of selenium in the range of 0.4–4.9 ppm and traces of copper and cobalt were detected from a part of the wheat samples.

The invention claimed is:

1. An apparatus for securing individual pieces of materials in a definite arrangement and a definite posture, comprising
    an energy ray-permeable holder provided with a plurality of receptacles disposed in a definite arrangement and a definite posture for receiving each individual piece of material the energy ray-permeable holder being provided over its surfaces with a reflective layer of a substance adapted to reflect the energy ray, and
    an energy ray-hardenable adhesive interposed between each individual piece of material and inner wall of the corresponding receptacle for fixing the material piece in the receptacle.

2. The apparatus as claimed in claim 1, wherein, when individual pieces of materials secured on the holder are to be analyzed by irradiation of an electromagnetic ray thereonto, the reflective layer on the holder comprises, at least on the side on which the electromagnetic ray is irradiated, a layer of a substance which will not cause analysis noise.

3. An apparatus for analyzing individual pieces of materials, comprising
    an apparatus for securing individual pieces of materials in a definite arrangement and a definite posture as claimed in claim 1 and
    an analyzing unit for analyzing each individual piece of material which has been secured on the holder.

4. An apparatus for sorting individual pieces of materials, comprising
    the apparatus for securing individual pieces of materials in a definite arrangement and a definite posture as claimed in claim 3, and
    the analyzing unit for analyzing individual pieces of material which has been secured on the holder as claimed in claim 3, and
    a sorting device operative to sort individual pieces of materials based on the results of the analyses.

5. A process for analyzing individual pieces of materials which have been secured at a definite posture in receptacles of an energy ray-permeable holder of an apparatus as claimed in claim 1, comprising the steps of
    forming on each individual piece of material an analyzing surface and
    performing the analysis by irradiation of an electromagnetic ray onto the analyzing surface.

6. The process as claimed in claim 5, wherein the analyzing surface consists of one or more planes which extend in horizontal and/or in any other inclined plane(s).

7. A process for securing individual pieces of materials in a definite arrangement and a definite posture, comprising the steps of
    receiving individual pieces of materials at a definite posture each piece being in one corresponding of a plurality of receptacles provided on an energy ray-permeable holder in a definite arrangement and a definite posture the energy ray-permeable holder being provided over its surfaces with a reflective layer of a substance adapted to reflect the energy ray, and
    bonding each individual piece of material onto an inner wall of the corresponding receptacle with an energy ray-hardenable adhesive by irradiating an energy ray onto the adhesive to harden it to thereby fix the material piece in the receptacle.

8. The process as claimed in claim 7, wherein, when individual pieces of materials secured on the holder are to be analyzed by irradiation of an electromagnetic ray thereonto, the reflective layer on the holder comprises, at least on the side on which the electromagnetic ray is irradiated, a layer of a substance which will not cause analysis noise.

9. A process for analyzing individual pieces of materials, comprising the step of
    performing the analysis for each individual piece of material which has been secured at a definite posture by the process as claimed in claim 7.

10. A process for sorting individual pieces of materials, comprising the step of
    performing sorting operations for each individual piece of material based on the results of analyses obtained by a process for analyzing individual pieces of materials as claimed in claim 9 and
    effecting multiplication and/or amplification of the sorted individual piece.

* * * * *